(12) United States Patent
Huang et al.

(10) Patent No.: US 7,862,783 B2
(45) Date of Patent: Jan. 4, 2011

(54) SEPARATION PROCESS FOR METHYL ACETATE HYDROLYSIS AND APPARATUS THEREOF

(75) Inventors: Hsiao-Ping Huang, Taipei (TW); Cheng-Ching Yu, Taipei (TW); Ming-Jer Lee, Taipei (TW); Yu-De Lin, Taipei (TW); Jian-Kai Cheng, Erlin Township, Changhua County (TW)

(73) Assignee: National Taiwan University, Taipei (TW)

( * ) Notice: Subject to any disclaimer, the term of this patent is extended or adjusted under 35 U.S.C. 154(b) by 991 days.

(21) Appl. No.: 11/699,849

(22) Filed: Jan. 30, 2007

(65) Prior Publication Data

US 2008/0128262 A1 Jun. 5, 2008

(30) Foreign Application Priority Data

Dec. 5, 2006 (TW) .............................. 95145254 A

(51) Int. Cl.
*B01J 8/02* (2006.01)
*B01D 3/00* (2006.01)

(52) U.S. Cl. ........................ 422/189; 422/190; 422/234; 422/235; 202/161; 203/29; 203/DIG. 6

(58) Field of Classification Search .................. 422/189, 422/190, 234, 235; 202/161; 203/29, DIG. 6
See application file for complete search history.

(56) References Cited

U.S. PATENT DOCUMENTS 2,936,321 A * 5/1960 Mercier ....................... 562/607
5,770,770 A * 6/1998 Kim et al. ................... 562/608
2002/0183549 A1 12/2002 Lee
2006/0128991 A1* 6/2006 Michl et al. ................. 562/606

OTHER PUBLICATIONS

Han, S. J., Y. Jin and Z. Q. Yu. "Application of a Fluidized Reaction-Distillation Column for Hydrolysis of Methyl Acetate", *Chem. Eng. Journal* 66 (1997), pp. 227-230.
Fuchigami, Yoshio. "Hydrolysis of Methyl Acetate in Distillation Column Packed with Reactive Packing of Ion Exchange Resin", *Journal of Chem. Eng. of Japan*, vol. 23, No. 3 (1990), pp. 354-359.

* cited by examiner

*Primary Examiner*—Jennifer A Leung
(74) *Attorney, Agent, or Firm*—Volpe & Koenig, P.C.

(57) ABSTRACT

A separation system for a methyl acetate hydrolysis is provided. The separation system comprises a reactive distillation system, a reflux system, a first separation system and a second separation. The reactive distillation system allows the hydrolysis of a methyl acetate solution to generate a first mixture and a second mixture. The reflux system is packed with a heterogeneous catalyst and coupled to the reactive distillation system, which refluxes the first mixture to the reactive distillation system. The first separation system is coupled to the reactive distillation system, which directs the second mixture thereinto so as to isolate an acetic acid and a third mixture therefrom. The second separation system is coupled to the first separation system, which directs the third mixture thereintio so as to separate a methanol therefrom. The methyl acetate feeding system is coupled to, one of the reactive distillation system and the reflux system, which feeds the methyl acetate solution thereinto.

11 Claims, 1 Drawing Sheet

SEPARATION PROCESS FOR METHYL ACETATE HYDROLYSIS AND APPARATUS THEREOF

FIELD OF THE INVENTION

The present invention relates to a separation process for an ester hydrolysis and the apparatus thereof, and more particularly to a separation process for a methyl acetate hydrolysis and the apparatus thereof to generate an acetic acid and a methanol with high purity.

BACKGROUND OF THE INVENTION

Polyvinyl alcohol is a kind of polymer widely used in the chemical industry; however, the manufacturing process of polyvinyl alcohol is always accompanying with the abundant production of a by-product, methyl acetate. Methyl acetate is a less valuable solvent due to its low industrial application and low volatility, even if the amount of the produced methyl acetate is one-half times higher than that of polyvinyl alcohol. Accordingly, the impure methyl acetate is usually discharged into the atmosphere after scrubbing in a wastewater treatment system or burned in an incinerator. In view of the above, if the methyl acetate could be recycled to be efficiently hydrolyzed into an acetic acid and a methanol, which are higher valuable solvents, the working performance of the polyvinyl alcohol plants will be highly increased.

Recently, reactive distillation processes, which both reaction and separation are carried out in the same column, have been developed for improving the efficiency of the hydrolysis reaction in conventional distillation processes of low yield of products, high fixed costs and high operating costs.

Fuchigami (1990) proposed that the hydrolysis of methyl acetate is performed within a single reactive distillation column in which the reactive distillation column is packed with 85% ion exchange resin (Amberlist® 15) and 15% polyethylene powders as catalysts. The reactive distillation column is devised to be divided into two portions in which the upper portion is considered as a reaction section and the lower portion is considered as a stripping section. Since the products formed on the top of the reactive distillation column are fully refluxed, the rectifying process is thus deemed negligible. There are two feeding streams in Fuchigami's reactive distillation process; one is the mixture of methyl acetate and methanol and the other is pure water, and they are respectively introduced into the top and the bottom of the reaction section. The hydrolysis reaction is controlled by the equilibrium constant, which the azeotropes formed by the unreacted methyl acetate and methanol tend to exist on the top of the column. As the result of Fuchigami's experimental results, it is known that the excess water and the full reflux will contribute to raise the conversion rate of the methyl acetate. However, the conversion rate of the methyl acetate is capable of achieving 98.4% only on condition that the molar ratio of methyl acetate to water is 11 and the reflux ratio is 2.16. By virtue of the foregoing, the excess water makes the respective amounts of the acetic acid and the methanol highly diluted, and the consumption of the excess water is uneconomical.

Han et al. (1997) proposed another reactive distillation scheme that an additional reactor of 2.5 liter is mounted ahead of the reactive distillation column. The reactive distillation column is devised to be divided into three portions, which are respectively the rectifying section, the reaction section and the stripping section. Water stream is firstly mixed with the methyl acetate in an excess amount, and then the mixture is fed to the reactor in which the mixture in the reactor is subsequently introduced to the lower part of the reaction section. Water stream is introduced to the upper of the reaction section, so that the feeding equivalent molar number of water and methyl acetate is able to be maintained. Furthermore, in order to increase the mass flow efficiency among the gaseous phase, the liquid phase and the solid catalysts, the reaction section are packed with the fluidifying filled bed and the selected catalysts are ion exchange resins. There are effluents formed on the top of the reactive distillation column, and parts of the effluents are refluxed to the reactive distillation column. The highest conversion rate of the methyl acetate is 50%, which is achieved only on condition that the reflux ratio is 1 and total feeding amount is 2 (L/hr). The conversion rate in the reactor only arrives at 20%, whereas the conversion rate in the reactive distillation column arrives at 30%. In view of the reactive distillation scheme proposed by Han et al., the additional reactor mounted ahead of the reactive distillation column seems failed to raise the conversion rate efficiently.

Lee (2002) proposed a composite reactive distillation process where the reflux drum in the conventional distillation tower is replaced with a fixed bed reactor packed with cation exchange resins (Amberlyst® 15 and Diaion® PK) as catalysts. The products on the top of the reactive distillation tower are fully condensed and then transferred into the reactor before the products are fed to the reactive distillation tower for further separation, so that the full refluxing of the top products are maintained. However, the considerable investing costs resulting from the amount of the required consuming steam and the packed catalysts are burdensome for most polyvinyl alcohol plants even if the quite high conversion rate of methyl acetate is achieved according to Lee et al.'s proposed composite structure.

In view of the mentioned drawbacks, a special reactive distillation process with the competitive investing costs and the higher conversion rate of methyl acetate is necessary for most polyvinyl alcohol plants and is economical.

From the above description, it is known that how to develop an improved reactive distillation process for methyl acetate hydrolysis has become a major problem to be solved. In order to overcome the drawbacks in the prior art, an improved separation system for methyl acetate hydrolysis is provided. The particular design in the present invention not only solves the problems described above, but also is easy to be implemented. Thus, the invention has the utility for the industry.

SUMMARY OF THE INVENTION

In consideration of a methyl acetate hydrolysis working in the polyvinyl alcohol plants with a more economic and efficient operation, a cost-saving separation system for methyl acetate is needed.

In accordance with one aspect of the present invention, a separation process for a hydrolysis of methyl acetate is provided, which comprises the following steps: (a) hydrolyzing a methyl acetate solution in a reactive distillation device to generate a first mixture and a second mixture; (b) condensing the first mixture and refluxing the condensed first mixture to the reactive distillation device via a reflux system packed with a heterogeneous catalyst; (c) directing the second mixture into a first separation device for an first distillation to isolate an acetic acid and a third mixture therefrom; and (d) condensing the third mixture and directing a first portion of the condensed third mixture to a second separation device for an second distillation to separate an methanol thereform.

In accordance with another aspect of the present invention, a separation device for hydrolyzing methyl acetate is provided. The separation device comprises a reactive distillation device, a reflux device, a first separation device and a second separation. The reactive distillation device provides a location for hydrolyzing a methyl acetate to generate a first mixture and a second mixture. The reflux device is packed with a heterogeneous catalyst and coupled to the reactive distillation device so as to reflux the first mixture to the reactive distillation device. The first separation is coupled to the reactive distillation device so as to direct the second mixture thereinto and isolate an acetic acid and a third mixture therefrom. The second separation is coupled to the first separation device to direct a first portion of the third mixture thereinto so as to separate a methanol therefrom.

In accordance with a further aspect of the present invention, a separation for a methyl acetate hydrolysis is provided. The separation system comprises a reactive distillation system, a reflux system, a first separation system, a second separation system and a methyl acetate feeding system. The methyl acetate hydrolysis is performed in the reactive distillation system and thus a first mixture and a second mixture are generated. The reflux system is packed with a heterogeneous catalyst and coupled to the reactive distillation system for refluxing the first mixture to the reactive distillation system. The first separation system is coupled to the reactive distillation system for directing the second mixture thereinto so as to isolate an acetic acid and a third mixture therefrom. The second separation system is coupled to the first separation system for directing a portion of the third mixture thereinto so as to separate a methanol therefrom. The methyl acetate feeding system is coupled to one of the reactive distillation system and the reflux system for feeding the methyl acetate thereinto.

The above aspects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

Figure 1:
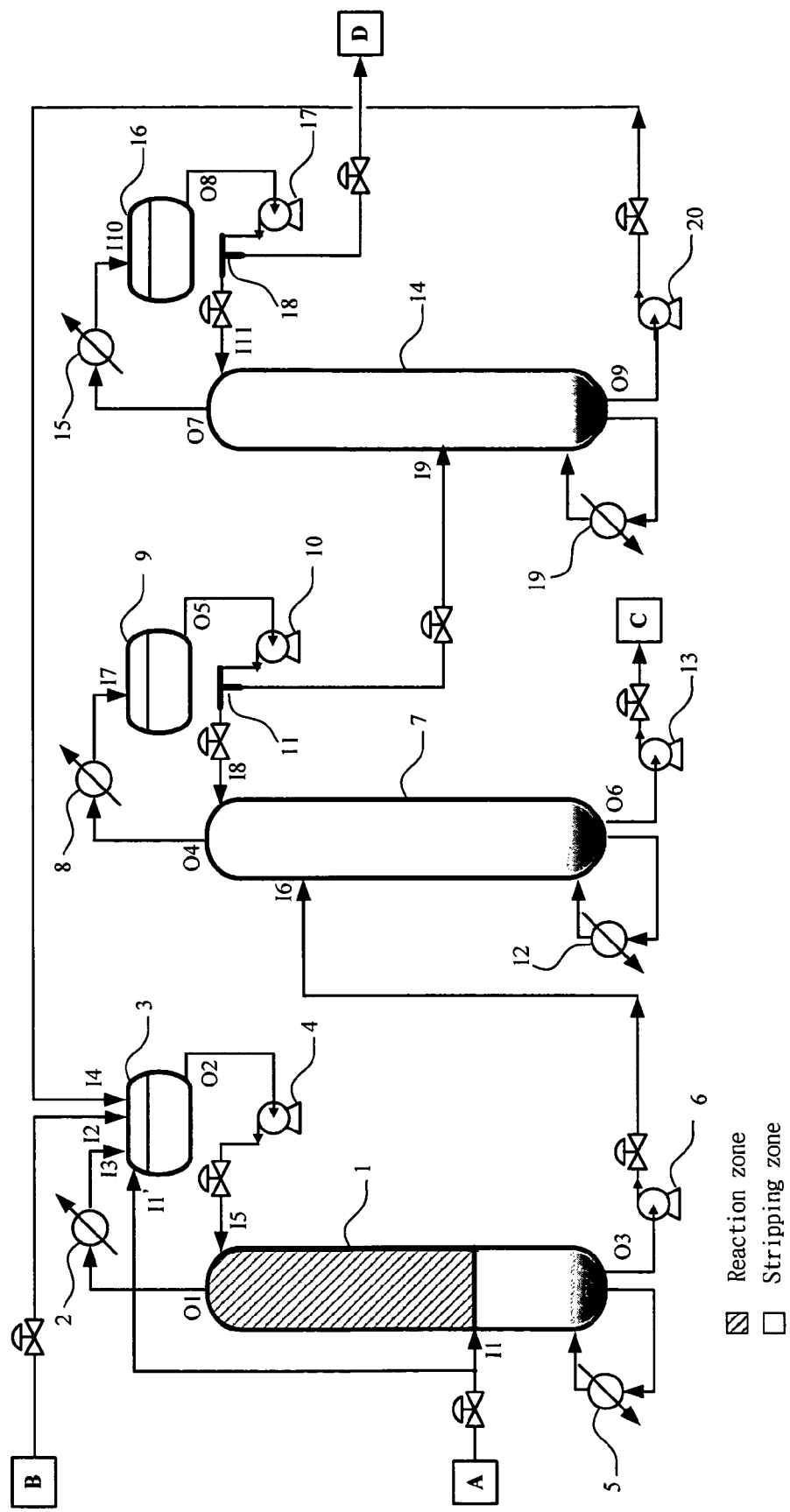
FIG. 1 is a schematic diagram of the separation system for a methyl acetate hydrolysis according to a preferred embodiment of the present invention.

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

A reaction formula of the methyl acetate hydrolysis is shown below:

MeAc+H$_2$O↔MeOH+HAc

The mentioned abbreviation "MeAc" represents methyl acetate; the abbreviation "MeOH" represents methanol; the abbreviation "HAc" represents acetic acid.

The hydrolysis of methyl acetate is a reversible reaction and possesses the low equilibrium constant. The feeding of Methyl acetate is regarded as a controlling limited factor in the separation system for methyl acetate hydrolysis, and thus the reaction will be towards the production of the hydrolyzed product provided that feeding the excess amount of water is performed continuously. Accordingly, it is preferred to feed the excess amount of water to promote the reaction towards hydrolyzing methyl acetate in the separation system for methyl acetate hydrolysis and apparatus of the present invention.

In consideration of the physical properties of the hydrolysis system for methyl acetate in its entirety, the priority of the boiling points of each constituent existing in the methyl acetate hydrolyzing system is shown in Table (I).

TABLE (I)

| Constituents | Boiling Point (° C.) |
|---|---|
| MeAc/MeOH | 53.6 |
| MeAc/H$_2$O | 56.4 |
| MeAc | 57.0 |
| MeOH | 64.7 |
| H$_2$O | 100.0 |
| HAc | 118.1 |

In the hydrolysis system of methyl acetate, the possible azeotropes include two binary-components, methyl acetate and methanol together with methyl acetate and water, where the co-boiling points between the two binary-components are very close. Furthermore, methyl acetate is the lightest component and easily tends to form the azeotrope with methanol. Consequently, it is better devised to recycle the effluent from the column top rather than to discharge the effluent, so that the composition ratio of methyl acetate within the column will be increased without losing from the column bottom, and thus such design will facilitate the hydrolysis reaction.

The catalysts required for the hydrolysis reaction could be one of the heterogeneous catalysts and homogeneous catalysts. In the separation system of the methyl acetate hydrolysis of the present invention, heterogeneous solid catalysts are utilized to promote the reaction. The solid catalysts superiors in the convenience that they be packed anywhere within the reactor (e.g. the bottom and the top thereof, the reflux device, etc.), so that the reaction section could be selected flexibly to be disposed within the reactor, and the problem to recycle the liquid catalyst could be solved accordingly.

Ion exchange resins are generally chosen as the solid catalysts, such as Amberlyst® 15 (Rohm and Hass) or Purolite CT179 (Purolite) commonly used in the industry. In addition, Katapak-S is commonly adopted as the packing structure of the solid catalysts or the packings of the solid catalysts are disposed within the trays via a fixed device (Davy Process Technology).

Please refer to FIG. 1, which depicts a schematic diagram of the separation process of the methyl acetate hydrolysis in the present invention, which comprises a reactive distillation system, a reflux system, a first separation system and a second separation system.

The reactive distillation system comprises a reactive distillation device (1), an input pipe (I1), another input pipe (I5), an output pipe (O1) and another output pipe (O3). The reactive distillation device (1) is devised to be divided into a reaction section and a stripping section (not shown in FIG. 1), wherein the reaction section are disposed with a plurality of reaction trays and the stripping area are disposed with a plurality of stripping trays (not shown in FIG. 1). The plurality of reaction trays are packed with ion exchange resins (Amberlyst® 15) for increasing the reaction efficiency thereof.

Furthermore, a re-boiling device (5) is disposed beneath the bottom of the reactive distillation device (1) to heat the liquid deposited on the bottom of the reactive distillation device (1). The reactive distillation device (1) allows the continuous proceeding of hydrolyzing the methyl acetate solution, whereby the existing components include methyl acetate, methanol, acetic acid and water after the hydrolysis. As the above, the methanol and the methyl acetate with the lower boiling points rise to the top of the reactive distillation device (1) since they are converted from a liquid phase to a gaseous one. Correspondingly, the acetic acid, the water and the methanol deposit on the bottom of the reactive distillation device (1) since the boiling points thereof are higher than that of the methyl acetate. Accordingly, due to the distinct borderline of the boiling points, the mixture deposited on the bottom of the reactive distillation device (1) is named as the first liquid mixture herein, and the unreacted methyl acetate and the excess amount of water will be formed on the top of the reactive distillation device (1), where the mixture on the top is named as the first gaseous mixture herein.

The separation system of the methyl acetate hydrolysis in the present invention further comprises a first condensing system. The first condensing system comprises a condenser (2) and the relevant connecting tubes, where the condenser (2) is coupled to the reactive distillation device (1), so as to liquefy the first gaseous mixture from the reactive distillation device (1).

The reflux system comprises a reflux device (3), a pump (4), an input pipe (I2), another input pipe (I3), a further input pipe (I4) and an output (O2). The first gaseous mixture is liquefied via the condenser (2) and then fed to the reflux device (3) via the input pipe (I3) after the first gaseous mixture is discharged via the output pipe (O1). The reflux device (3) is also packed with the same ion exchange resins and an excess of water is fed thereto via the input pipe (I2), so that the liquefied and unreacted methyl acetate is capable of proceeding the hydrolysis continuously within the reflux device (3). The reacted product from the reflux device (3) is discharged via the output pipe (O2) by the pump (4) and then sent to the reactive distillation device (1) via the input pipe (I5).

The methyl acetate solution is fed to the reactive distillation device (1) via the input pipe (I1) from a methyl acetate solution tank (A) or alternatively fed to the reflux device (3) via an input pipe (I1') prior to fed to the reactive distillation device (1).

The first separation system comprises a first separation device (7), an input pipe (I6), another input pipe (I8), an output (O4) and another output pipe (O6). The first liquid mixture deposited on the bottom of the reactive distillation device (1) is discharged via the output pipe (O3) by the pump (6) and then fed to the first separation device (7) via the input pipe (I6).

Moreover, a re-boiling device (12) is disposed beneath the bottom of the first separation device (7) to heat the liquid deposited on the bottom of the first separation (7). The first liquid mixture within the first separation device (7) is re-boiled continuously, so that the methanol and the methyl acetate with the lower boiling points will be converted to a gaseous phase to rise to the top of the first separation device (7), whereby such process makes the acetic acid solution deposited on the bottom achieve a higher purity continuously. The acetic acid solution with higher purity is discharged via the output pipe (O6) by the pump (13) and then sent to an acetic acid reservoir (C). The compositions of the gaseous mixture risen to the top of the first separation device (7) are respectively the acetic acid and the methyl acetate in a rare amount together with the methanol and water in a huge amount.

The separation system of a methyl acetate hydrolysis in the present invention further comprises a second condensing system. The second condensing system comprises a condenser (8) and the relevant connecting tubes, where the condenser (8) is coupled to the first separation device (7), so as to liquefy the gaseous mixture from the first separation device (7).

Furthermore, the separation system of the methyl acetate hydrolysis in the present invention further comprises a first bypassing system. The bypassing system comprises a bypassing device, a pump (10), an input pipe (I7) and an output pipe (O5). Preferably, the bypassing system further comprises a reflux device (9) and a T-type bypassing device (11), wherein the reflux device (9) is coupled both to the condenser (8) and the T-type bypassing device (11). Subsequently, the gaseous mixture from the first separation device (7) is sent to the reflux device (9), so that the gaseous mixture is liquefied in the condenser (8) and then sent to the reflux device (9) via the input pipe (I7). The liquefied mixture in the reflux device (9) is discharged via the output pipe (O5) by the pump (10) and then sent to the T-type bypassing tube (11). The T-type bypassing device (11) further bypasses the mixture from the reflux device (9) into two portions, the first portion and the second portion. The first portion of the mixture from the reflux device (9) comprises the methanol with higher purity, and then is sent to the second separation device (10), whereas the second portion thereof is recycled to the first separation device (7).

The second separation system comprises a second separation device (14), an input pipe (I9), an input pipe (I11), an output pipe (O7) and another output pipe (O9). The first portion of the mention mixture having the methanol with higher purity is sent to the second separation device (14) via the input pipe (I9) for further separating procedure. In addition, a re-boiling device (19) is disposed beneath the bottom of the second separation device (14) to heat the liquid on the bottom of the second separation device (14). The composition ratio of the methanol in the gaseous mixture risen to the top of the second separation device (14) will be increased continuously by the heating process of the re-boiling device (19), whereas the mixture deposited on the bottom of the second separation device (14) will be discharged via the output pipe (O9) and then recycled to the reflux device (3) via the input pipe (I4) by the pump (20).

The separation system of the methyl acetate hydrolysis in the present invention further comprises a third condensing system. The third condensing system comprises a condenser (15) and the relevant connecting tubes, where the condenser (15) is coupled to the second separation device (14), so as to liquefy the liquid mixture having the methanol with higher purity from the second separation device (14).

Furthermore, the separation system of the methyl acetate hydrolysis in the present invention further comprises a second bypassing system. The second bypassing system comprises a bypassing device, a pump (17), an input pipe (I10), and an output pipe (O8). Preferably, the bypassing device further comprises a reflux device (16) and a T-type bypassing device (18), wherein the reflux device (16) is coupled both to the condenser (15) and the T-type bypassing device (18). The gaseous mixture having the methanol with higher purity is liquefied in the condenser (15) and is sent to the reflux device (16) via the input pipe (I10). The liquefied mixture in the reflux device (16) is discharged by the pump (17) and then sent to the T-type bypassing tube (18). The liquefied mixture in the T-type bypassing tube (18) is bypassed into two portions. As the above, the portion having the methanol with high purity is sent to a methanol reservoir (D), whereas the other portion is recycled to the second separation device (14).

The temperature of the different sections of the reactive distillation device (1) varies with the amount of the feeding streams and is controlled by the re-boiling device disposed on the bottom thereof. Similarly, the respective temperatures of the different sections existing in the first separation device (7) and the second separation device (14) are also controlled in the same way.

For saving the investing production cost, in the separation system of the methyl acetate hydrolysis of the present invention, the packed range of the solid catalysts in the reactive distillation device (1) is either from the top to the middle portion thereof or from the top to the lower portion thereof. In addition, the amount of the catalyst intended to be packed with the reflux device (3), which is coupled to the reactive distillation device (1), is one to ten times higher than that packed on the reactive trays within the reactive distillation device (1), or even one to one hundred times higher. In the present invention, the utilized catalyst is Amerlyst® 15 sold by Rohm and Hass™ which is commonly used in the industry.

According to the preferred embodiments of the present invention, the operating temperature in the reactive distillation device (1) is in a range from 55° C. to 115° C. Besides, the operating temperature in the first separation device (7) is in a range from 80° C. to 130° C., and the operating temperature existing in the second separation device (14) is in a range from 55° C. to 115° C. Furthermore, the operating pressure of the reactive distillation device (1), the first separation device (7) and the second separation device (14) is in a range from 1 to 2 atmosphere pressure, whereas the reflux devices (3), (9) and (16) are operated under the constant atmosphere pressure.

In the present invention, the number of the theoretical trays of the reactive trays in the reactive distillation device (1) is in a range from 5 to 15, and the number of the theoretical trays of the stripping trays therein is in a range from 8 to 30. In addition, the number of the theoretical trays in the first separation device (7) is in a range from 10 to 25, and the number of the theoretical trays in the second separation device (14) is in a range from 20 to 35.

| [Embodiments] | | |
|---|---|---|
| Items | Embodiment I | Embodiment II |
| Composition of the methyl acetate solution | Pure methyl acetate | 60% methyl acetate + 40% methanol |
| The reactive distillation device | | |
| No. of the reactive trays | 18 | 22 |
| No. of the stripping trays | 11 | 9 |
| No. of trays that pure water feeds | 30th | 32th |
| No. of trays that methyl acetate feeds | 6th | 32th |
| No. of trays that the reflux device refluxes to | 30th | 32th |
| The first separation device | | |
| No. of total trays | 15 | 16 |
| No. of plats for feeding | 14th | 14th |
| The second separation device | | |
| No. of total trays | 27 | 30 |
| No. of plats for feeding | 11th | 12th |
| The amount of reflux | 240 (kmol/hr) | 220 (kmol/hr) |
| The purity of acetic acid | 99 mol % | 99 mol % |
| The purity of methanol | 99 mol % | 99 mol % |

P.S. The reflux stream is introduced from the bottom of the second separation (14) to the reflux device (3).

In conclusion, although the reactive distillation system depends upon the plurality of the reactive trays and the plurality of the stripping trays to serve as the major reactive sections, the plurality of the reactive trays and the plurality of the stripping trays are alternatively capable of being disposed independently and coupled to the reactive distillation device. As described above, the working performance disclosed in the present invention will not be specifically limited to the disclosed embodiments therein, and all the separation systems by means of the mentioned reactive distillation system, the reflux system, the first separation system and the second separation system and their equivalents for hydrolyzing methyl acetate will not go beyond the protecting scope of the present invention.

As compared with the composite reactive distillation system proposed by Lee et al., the separation system for hydrolyzing methyl acetate in the present invention not only reduces the amount of the required steam and the amount of the catalysts required to be packed, but also enhances the economic value thereof.

Therefore, the present invention proposes an industrially applicable separation system of the methyl acetate hydrolysis in consideration of the thermodynamic properties of the hydrolysis system. According to the present invention, an acetic acid with 99 mol % high purity and a methanol with 99 mol % high purity are obtained together with low economic costs.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A separation apparatus for a methyl acetate hydrolysis, comprising:
    a reactive distillation device hydrolyzing a methyl acetate solution and generating a first mixture and a second mixture;
    a reflux device filled with a heterogeneous catalyst, coupled to the reactive distillation device and refluxing the first mixture to the reactive distillation device;
    a first separation device coupled to the reactive distillation device, and isolating an acetic acid and a third mixture from the second mixture; and
    a second separation device coupled to the first separation device and the reflux device, isolating a methanol from the third mixture, and having a bottom and a pipe located at the bottom and connected to the reflux device, wherein the second separation device discharges a fourth mixture at the bottom to the reflux device through the pipe.

2. A separation apparatus as claimed in claim 1, further comprising a condensing device disposed on a top of one device selected from a group consisting of the reactive distillation device, the first separation device and the second separation device.

3. A separation apparatus as claimed in claim 1, wherein the reactive distillation device comprises a plurality of reactive trays and a plurality of stripper trays.

4. A separation apparatus as claimed in claim 3, wherein the plurality of stripper trays are disposed on a lower portion of the reactive distillation device.

5. A separation apparatus as claimed in claim 3, wherein the plurality of reactive trays are disposed on an upper portion of the reactive distillation device.

6. A separation apparatus as claimed in claim 3, wherein a number of the plurality of the stripper trays is in a range from 5 to 15 and a number of the plurality of the reactive trays is in a range from 8 to 30.

7. A separation apparatus as claimed in claim 1, further comprising at least one boiling device disposed on a bottom of one device selected from a group consisting of the reactive distillation device, the first separation device and the second separation device.

8. A separation apparatus as claimed in claim 1, further comprising an acetic acid reservoir connected with a bottom of the first separation device, and a methanol reservoir connected with the second separation device.

9. A separation apparatus as claimed in claim 1, further comprising at least another reflux device disposed on a top of one of the first separation device and the second separation device.

10. A separation system for a methyl acetate hydrolysis, comprising:
   a reactive distillation system hydrolyzing a methyl acetate solution and generating a first mixture and a second mixture;
   a reflux system filled with a heterogeneous catalyst, coupled to the reactive distillation system, and refluxing the first mixture to the reactive distillation system;
   a first separation system coupled to the reactive distillation system, and isolating an acetic acid and a third mixture from the second mixture;
   a second separation system coupled to the first separation system and the reflux system, separating a methanol from the third mixture, and having a bottom and a pipe located at the bottom and connected to the reflux system, wherein the second separation device discharges a fourth mixture at the bottom to the reflux system through the pipe; and
   a methyl acetate feeding system coupled to one of the reactive distillation system and the reflux system for feeding the methyl acetate solution thereinto.

11. A separation system as claimed in claim 10, wherein the reactive distillation system is performed at a temperature in a range from 55 to 110° C., the first separation system is performed at a temperature in a range from 80 to 130° C. and the second separation system is performed at a temperature in a range from 55 to 115° C.

* * * * *